US006399793B1

(12) United States Patent
Kronenthal et al.

(10) Patent No.: US 6,399,793 B1
(45) Date of Patent: Jun. 4, 2002

(54) PROCESS FOR THE PREPARATION OF α' CHLOROKETONES

(75) Inventors: David Kronenthal, Yardley; Mark D. Schwinden, Newtown, both of PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/908,516

(22) Filed: Jul. 18, 2001

Related U.S. Application Data

(60) Provisional application No. 60/225,711, filed on Aug. 16, 2000.

(51) Int. Cl.$^7$ .................. C07D 301/02; C07C 221/00

(52) U.S. Cl. ........................... 549/519; 564/502

(58) Field of Search ................ 564/502; 549/519

(56) References Cited

U.S. PATENT DOCUMENTS 5,767,316 A * 6/1998 Honda et al. ............... 564/502
5,849,911 A 12/1998 Fassler et al. .............. 544/335

OTHER PUBLICATIONS

H. Konig and H. Metzger, Chem. Ber., 98, pp. 3733–3747, 1965.
J. I. DeGraw and M. Cory, Tetrahedron Letters, No. 20, pp. 2501–2502, 1968.
J. C. Powers and P. E. Wilcox, J. Am. Chem. Soc., 92, pp. 1782–1783, 1970.
C. J. Kowalski et al, J. Org. Chem., 50, pp. 5140–5142, 1985.
J. E. Baldwin et al, Synlett, pp. 51–53, 1993.
P. Chen, et al, Tetrahedron Letters, 38(18), pp. 3175–3178, 1997.
C. J. Kowalski, et al, J. Org. Chem., 57(26), pp. 7194–7208, 1992.

* cited by examiner

*Primary Examiner*—Amelia Owens
(74) *Attorney, Agent, or Firm*—David M. Morse

(57) ABSTRACT

The present invention relates to a process for the preparation of α' chloroketones, such as 4-phenyl-3-t-butyloxycarbonylamino)-2-keto-1-chlorobutane by reacting certain aryl amino acid esters, e.g. N-(2-t-butoxycarbonyl)-L-phenylalanine-4-nitrophenyl ester, with a sulfur ylide compound to form the corresponding keto ylide compound which is then treated with a source of chloride and an organic acid.

17 Claims, No Drawings

PROCESS FOR THE PREPARATION OF α' CHLOROKETONES

CROSS-REFERENCE TO RELATED APPLICATIONS

This application claims the benefit of U.S. Provisional Application Ser. No. 60/225,711 filed Aug. 16, 2000.

FIELD OF THE INVENTION

The present invention relates to a novel process for the preparation of α'-N-acyl-α'-chloroketones. The α'-chloroketones produced in accordance with the process of the invention are precursors of hydroxyethylamine isostere sub-units present in many molecules therapeutically useful as inhibitors of angiotensin converting enzyme, renin and HIV-protease.

BACKGROUND OF THE INVENTION

A process for preparing α-haloketones is described by König and Mezger in *Chem. Ber.,* Vol. 98, pages 3733–3747, 1965. The disclosed process involves the reaction of dimethyl-oxo-sulfoniummethylide with isocyanates and ketenes to form β-keto-sulfoniummethylides. On page 3738, in Table 3, there is disclosed treatment of the β-keto-sulfoniummethylides with hydrochloric acid or bromine to form α-chloroketone or α,α-dibromoketone.

Degraw and Cory, *Tetrahedron Letters,* No. 20, pages 2501—2501, 1968, disclose the preparation of α-acetoxy and α-halomethylketones from acyloxosulfonium ylides by the action of acids. This paper also teaches that the selective preparation of α-halo and α-acetoxymethyl ketones by the reaction of halogen acids or organic acids with α-diazoketones is well known. Given that the diazoketones are usually obtained by the reaction of diazomethane with the appropriate acid chloride, the method taught by this paper is not considered attractive for large-scale applications.

Powers and Wilcox, *J. Am. Chem. Soc.,* 92, page 1782, 1970 describe a classical method for the preparation of α-chloroketones involving the conversion of an N-acyl-α-amino acid to a α-diazoketone and subsequent acidolysis with HX. The use of diazomethane in this method makes it impractical for large-scale operations and also imposes safety considerations.

Kowalski et al., *J. Org. Chem.,* Vol. 50, 5140, 1985 and *J. Org. Chem.,* Vol. 57, 7194, 1992, describe homologation of esters to α-bromoketones utilizing the reagent system $CH_2Br_2/LDA/n$-BuLi.

Baldwin et al., *Synlett,* pages 51–53, 1993 describe a process whereby a nucleophilic ring compound, an activated monocyclic β-lactam, is opened by reaction with trimethylsulfoxonium ylide, lithiated sulfones and cuprates to form a variety of functionalized γ-keto-α-amino acids that are useful intermediates for the synthesis of natural products.

Chen and Cheng, *Tetrahedron Letters,* Vol. 38, No. 18, pages 3175–3178, 1997, describes the development of reactions for the preparation of α-chloroketones and proposes a practical process for the preparation of α'-chloroketones of N-carbamate-protected α-amino acids by reaction of lithium diisopropylamide and chloroiodomethane with BOC-L-phenylalanine ethyl ester. This process, however, is disadvantageous in that there is formed the high-boiling, toxic by-product chlorodiiodomethane.

SUMMARY OF THE INVENTION

The present invention is directed to an improved process for the preparation of α-N-acyl-α'-chloroketones by the action of a sulfur ylide on aryl esters to generate a keto ylide that is in turn treated with a source of chloride and an organic acid. The present invention is further directed to an improved process for the preparation of corresponding epoxide compounds that are intermediates in the synthesis of an important HIV protease inhibitor.

DETAILED DESCRIPTION OF THE INVENTION

The process of the present invention provides an advantageous synthesis for the α-N-acyl-α'-chloroketones represented by the formula

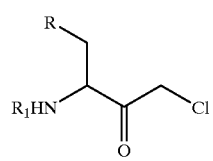

I wherein R is selected from the group consisting of alkyl, substituted alkyl, aryl and substituted aryl and $R_1$ is a protecting group for the amino function.

The compounds represented by formula I are irreversible enzyme inhibitors and are also useful as intermediates in the synthesis of molecules that are inhibitors of ACE, renin and HIV proteases. Such compounds and their use are disclosed, for example, in U.S. Pat. No. 5,849,911, the disclosure of which is incorporated herein by reference.

As utilized herein, the following terms have the definitions given below. The term "alkyl" refers to optionally substituted straight- or branched-chain saturated hydrocarbon groups having from 1 to 7 carbon atoms, preferably from 1 to 4 carbon atoms. The expression "lower alkyl" refers to optionally substituted alkyl groups having from 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino and disubstituted amino. The definitions given herein for alkyl and substituted alkyl apply as well to the alkyl portion of alkoxy groups.

The term "aryl" refers to monocyclic or bicyclic aromatic hydrocarbon groups having from 6 to 12 carbon atoms in the ring portion, for example, phenyl, naphthyl, biphenyl and diphenyl groups, each of which may be substituted.

The term "aralkyl" refers to an aryl group bonded to a larger entity through an alkyl group, for example, a benzyl radical.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocylooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "protecting group on the amino function" refers to an art-recognized group of moieties that can be attached to an amino group to keep it from being involved in reactions taking place elsewhere on the moiety to which it is attached. Preferred among such groups is t-butoxycarbonyl (BOC), but art-recognized amino function protecting groups, generally alkoxycarbonyl or aryloxycarbonyl groups, such as benzyloxycarbonyl, can be used as well.

The starting materials for the process of preparing α-chloroketones in accordance with the present invention are aryl esters represented by the formula

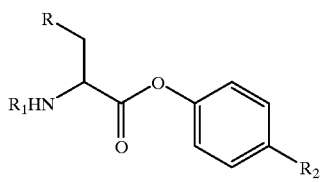

II wherein R and $R_1$ are as defined above and $R_2$ is hydrogen or nitro and may be substituted in the ortho or para position on the phenyl ring. The compounds represented by formula II are commercially available or can be prepared by techniques well known to those of ordinary skill in the art. The protecting group on the amino function is preferably t-butoxycarbonyl (BOC), but can also be other art-recognized amino function protecting groups as discussed above.

In accordance with the process of the present invention, the starting material represented by formula II above is treated with a sulfur ylide, i.e. a compound containing a function represented by the formula

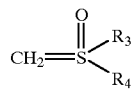

to produce an intermediate keto ylide compound represented by the formula

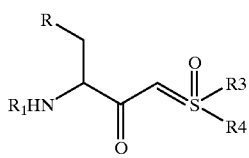

III wherein R and $R_1$ are as defined above and $R_3$ and $R_4$ are selected from the group consisting of alkyl, substituted alkyl and aryl. The sulfur ylide reagent is conveniently prepared from a sulfoxonium salt by reaction with a suitable base in an organic solvent. Suitable sulfoxonium compounds include trialkyl sulfoxonium halides, such as trimethylsuloxonium iodide. Preferable bases include, for example, sodium hydride, potassium tert. butoxide and potassium tert. amylate, with the latter being particularly preferred. The reaction is carried out in an organic solvent such as dimethylformamide, tetrahydrofuran or, preferably, toluene with mild heating, i.e. at a temperature of from about 60° C. to about 80° C., preferably about 70° C.

Once the sulfur ylide reagent is formed, it is reacted with the starting material represented by formula II above, optionally in the presence of a co-solvent. As an example of the use of a mixed solvent reaction medium, the reaction of the trialkylsulfoxonium compound and base is carried out in toluene as described, the resulting solution is cooled to about 0° C., and then added to a solution of the starting material in tetrahydrofuran to form the keto ylide intermediate compound represented by formula III above.

The keto ylide compound represented by formula III is then converted to the subject α-N-acyl-α'-chloroketones by reaction with a source of chloride, preferably a basic source of chloride, most preferably lithium chloride, and an organic acid, for example, methanesulfonic acid. The treatment with the source of chloride is carried out in an organic solvent, such as tetrahydrofuran, toluene or, preferably, acetonitrile. The reaction is initiated at low temperature, i.e. from about 0° C. to about 5° C. As the reaction proceeds, however, the temperature is raised to about 65° C. Reaction of the keto ylide represented by formula III above with a quaternary chloride, such as tetrabutylammonium chloride, yields a mixture of products resulting from competitive dealkylation.

The α-N-acyl-α'-chloroketones represented by formula I above, in addition to their own activity as irreversible enzyme inhibitors, are important intermediates in the synthesis of molecules that are inhibitors of ACE, renin and HIV proteases. The activity of such molecules against HIV proteases makes them very valuable in the treatment of retroviral infections such as AIDS. Specifically, the α-N-acyl-α'-chloroketones represented by formula I are converted by reduction either chemically or enzymatically to an intermediate represented by the formula IV that is, in turn treated with a suitable base to convert it to the corresponding epoxide represented by formula V as shown below

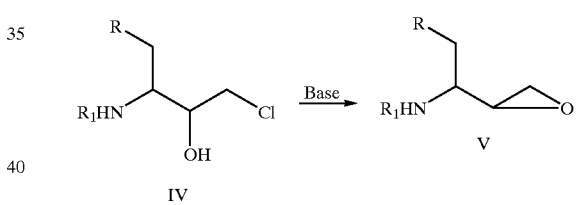

The epoxide compounds represented by formula V are intermediates that can be converted to the important HIV protease inhibitor 2,5,6,10,13-pentaazaretetradecanedioic acid, 3,12-bis(1,1-dimethylethyl)-8-hydroxy-4,11-dioxo-9-(phenylmethyl)-6{[4-(2-pyridinyl)phenyl]methyl}-dimethyl ester (3S,8S,9S,12S) as disclosed in U.S. Pat. No. 5,849,911, the disclosure of which is incorporated herein by reference. The synthesis of the compounds represented by formula V above beginning with the compound represented by formula II is an improvement over synthetic routes known heretofore.

It is understood that various other embodiments and modifications in the practice of the invention will be apparent to, and can be readily made by, those of ordinary skill in the art without departing from the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the relevant art. The invention is further described with reference to the following experimental work.

EXAMPLE 1

Preparation of (3S)-2-oxo-3-(t-butyloxycarbonylamino)-4-phenylbutylide dimethylsulfoxonium A one liter flask equipped with a large stir bar, a reflux condenser and an argon inlet was charged with trimethylsulfoxonium iodide (35.3 g, 160.5 mmol) and tetrahydrofuran (200 mL). There was then added with stirring 88 mL of a 25 wt % solution of potassium t-amylate in toluene (176.0 mmol) and the reaction was stirred at 70° C. for two hours to afford the corresponding ylide which was reacted in solution without isolation. The reaction mixture was cooled to 1° C. and a solution of N-(2-t-butoxycarbonyl)-L-phenylalanine-4-nitrophenyl ester (20.0 g, 51.8 mmol) in 80 mL of tetrahydrofuran was added via cannula over 15 minutes so that the internal temperature remained between 1° and 5° C. The reaction was stirred at this temperature for about five minutes and then was allowed to warm to ambient temperature over 30 minutes. The reaction mixture was stirred at ambient temperature for a further 30 minutes. HPLC analysis of an aliquot of the reaction mixture diluted with 1 mL of acetonitrile and 5 drops of water showed complete consumption of the N-t-butoxycarbonyl-L-phenylalanine-4-nitrophenyl ester.

The reaction mixture was quenched with 100 mL of water and stirred for 15 minutes after which it was concentrated under vacuum to remove organic solvents. The concentrated mixture was diluted with a further 550 mL of water and extracted with one 200 mL portion and two 100 mL portions of dichloromethane. The combined extracts were washed with two 200 mL portions of water, dried over magnesium sulfate and concentrated under vacuum. The residual solvents were removed under high vacuum for 30 minutes to obtain the product as a light yellow solid (17.4 g., 99%) which was carried on to Example 2 without further purification.

EXAMPLE 2

Preparation of (S)-[N-(1-benzyl-2-oxo-3-chloro)propyl]carbamic acid t-butyl ester A one liter flask equipped with a large stir bar, a reflux condenser and an argon inlet was charged with (3S)-2-oxo-3-(t-butyloxycarbonylamino)-4-phenylbutylide dimethylsulfoxonium (17.0 g, 50.0 mmol) and 250 mL of tetrahydrofuran. The mixture was cooled to 1° C. and lithium chloride (2.55 g, 60.1 mmol) was added in a single portion (the internal temperature of the reaction mixture rose to 2° C). Methanesulfonic acid (3.6 mL, 55.1 mmol) was added over five minutes so that the internal temperature of the mixture remained between 1° C. and 3° C., after which the mixture was stirred at 65° C. for four hours. The reaction mixture stirred as a very thick slurry for the first thirty minutes of this period. HPLC revealed complete consumption of the starting material and formation of (S)-[N-(1-benzyl-2-oxo-3-chloro)propyl]carbamic acid t-butyl ester. The reaction was allowed to cool to ambient and concentrated under vacuum to a solid/oil mixture. The mixture was taken up in 170 mL of ethyl acetate, washed with 80 mL of half-saturated aqueous sodium bicarbonate and 80 mL of saturated aqueous sodium chloride, dried over magnesium sulfate, filtered and concentrated under vacuum. The residual solvents were removed under high vacuum overnight to obtain (S)-[N-(1-benzyl-2-oxo-3-chloro)propyl]carbamic acid t-butyl ester as a crude product, 14.5 g, 97%, as a light yellow solid. A 500 mL flask with a large stir bar and a reflux condenser was charged with crude product, 14.25 g, and 210 mL of hexanes. The mixture was stirred at reflux and 10 ml of methyl t-butyl ether was added to dissolve the solid. The solution was allowed to cool to ambient temperature over one hour. The solution became cloudy and then turned into a very thick slurry which was stirred for two hours. The product was collected by filtration and washed with 25 mL of hexanes followed by 35 mL of hexanes. The product was air-dried for one hour to afford 11.9 g of (S)-[N-(1-benzyl-2-oxo-3-chloro)propyl]carbamic acid t-butyl ester, 81% overall yield, as an off-white solid.

EXAMPLE 3

Preparation of (S,S)-[N-(1-benzyl-2-hydroxy-3-chloro)propyl]carbamic acid t-butyl ester.

A solution of (S)-[N-(1-benzyl-2-oxo-3-chloro)propyl]carbamic acid t-butyl ester prepared in Example 2 (5 g, 16.8 mmol) in 84 mL of tetrahydrofuran and 9 mL of water is treated with sodium borohydride (1.59 g, 42 mmol) at 0° C. The temperature is maintained with stirring for 45 minutes, after which the reaction mixture is concentrated to dryness. The residue is stirred at 0° C. with a mixture of 150 mL of ethyl acetate and 25 mL of water while saturated potassium bisulfite solution is carefully added until the pH of the mixture reaches about pH 1.5. The resulting mixture is diluted with 350 mL of ethyl acetate and the layers separated. The organic layer is washed with water and brine, dried over magnesium sulfate and concentrated to a white solid. The material is recrystallized from hot ethyl acetate to afford (S,S)-[N-(1-benzyl-2-hydroxy-3-chloro)propyl] carbamic acid t-butyl ester (2.57 g, 50%). The minor amount of the (S,R) diastereomer is isolated from the mother liquor.

EXAMPLE 4

Preparation of 1-(1'(R)-oxiranyl)-2-(phenylethyl) carbamic acid t-butyl ester.

A 10 mL flame-dried flask equipped with a stir bar and an argon inlet was charged with (S,S)-[N-(1-benzyl-2-hydroxy-3-chloro)propyl]carbamic acid t-butyl ester as prepared in Example 3 (200 mg, 0.67 mmol), isopropanol (3.6 mL) and tetrahydrofuran (1 mL). The solution was cooled to 16° C. and potassium tert-butoxide (79 mg. 0.67 mmol) was added in one portion. The reaction was stirred at approximately 17° C. for 30 minutes. Acetic acid (3 drops) was added thereto and the mixture was concentrated to a solid/liquid mixture. The mixture was taken up in methyl, tert. butyl ether (10 mL) and washed with water (5 mL), saturated sodium hydrogen carbonate solution (1.5 mL), half-saturated sodium hydrogen carbonate solution (1.5 mL) and saturated sodium hydrogen carbonate solution (1.5 mL). The resultant organic layer was dried with magnesium sulfate, filtered and concentrated to afford 1-(1'(R)-oxiranyl)-2-(phenylethyl) carbamic acid t-butyl ester (170 mg., 96%) as a light-yellow oil which solidified at room temperature.

We claim:

1. A process for the preparation of α-N-acyl-α'-chloroketones represented by the formula

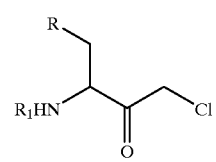

I wherein R is selected from the group consisting of alkyl, substituted alkyl, aryl and substituted aryl and $R_1$ is a protecting group for the amino function comprising reacting aryl esters represented by the formula

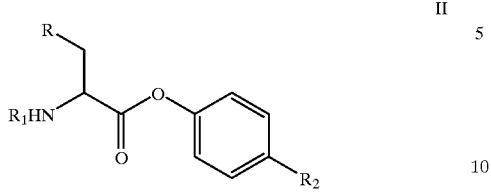

wherein R and $R_1$ are as defined above and $R_2$ is hydrogen or nitro and may be substituted in the ortho or para position on the phenyl ring with a compound containing a function represented by the formula

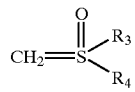

wherein $R_3$ and $R_4$ are selected from the group consisting of alkyl, substituted alkyl and aryl, to produce an intermediate keto ylide compound represented by the formula

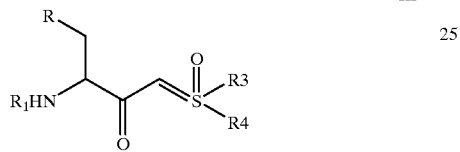

and treating said compound represented by formula III with a source of chloride and an organic acid.

2. A process in accordance with claim 1, wherein R is phenyl and $R_1$ is t-butoxycarbonyl.

3. A process in accordance with claim 1, wherein $R_2$ is nitro and is substituted in the para position on the phenyl ring.

4. A process in accordance with claim 1, where $R_3$ and $R_4$ are each methyl.

5. A process in accordance with claim 1, additionally including the step of forming said sulfur ylide compound by the reaction of a sulfoxonium compound with a base in an organic solvent.

6. A process in accordance with claim 5, wherein said sulfoxonium compound is a trialkyl sulfoxonium halide and said base is potassium tert.-amylate.

7. A process in accordance with claim 1, wherein the reaction of said compound represented by formula II with said sulfur ylide compound is carried out in an organic solvent at a temperature of from about 60° C. to about 80° C.

8. A process in accordance with claim 6, where said solvent is at least one member selected from the group consisting of dimethylformamide, tetrahydrofluran and toluene.

9. A process in accordance with claim 1, wherein said source of chloride is lithium chloride.

10. A process in accordance with claim 1, wherein said organic acid is methanesulfonic acid.

11. A process in accordance with claim 1, wherein the reaction of said keto ylide compound represented by formula III with the source of chloride and the organic acid is initiated at a temperature of from about 0° C. to about 5° C. in an organic solvent.

12. A process in accordance with claim 11, wherein said solvent is tetrahydrofuran.

13. A process of preparing an epoxy compound represented by the formula

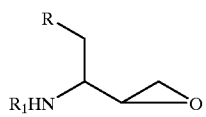

wherein R is selected from the group consisting of alkyl, substituted alkyl, aryl and substituted aryl and $R_1$ is a protecting group for the amino function, comprising reacting an aryl ester represented by the formula

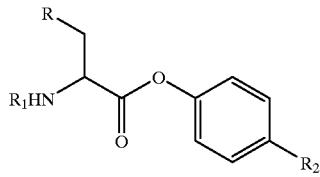

wherein R and $R_1$ are as defined above and $R_2$ is hydrogen or nitro and may be substituted in the ortho or para position on the phenyl ring with a compound containing a function represented by the formula

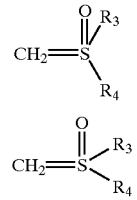

wherein $R_3$ and $R_4$ are selected from the group consisting of alkyl, substituted alkyl and aryl to produce an intermediate keto ylide compound represented by the formula

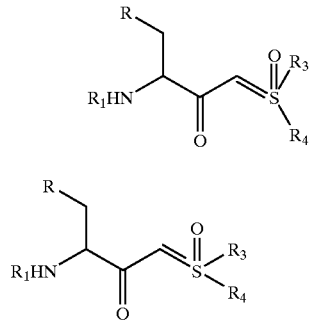

wherein R, $R_1$, $R_3$ and $R_4$ are as defined above, treating said compound represented by formula III with a source of chloride and an organic acid to form a 1-substituted-2-amino-3-oxo-4-chloro butane compound represented by the formula

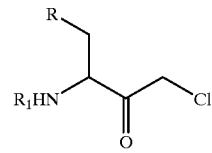

wherein R and $R_1$ are as defined above, reducing said compound to form a 1-chloro-2-hydroxy-3-amino-4-substituted butane compound represented by the formula

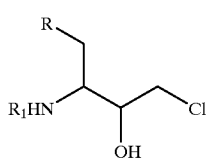

wherein R and $R_1$ are as defined above and reacting said hydroxy compound with a base to form said epoxy compound.

14. A process in accordance with claim 13, wherein R is phenyl and $R_1$ is t-butyloxycarbonyl.

15. A process in accordance with claim 13 wherein $R_2$ is nitro and is substituted in the para position on the phenyl ring.

16. A process in accordance with claim 13, where $R_3$ and $R_4$ are each methyl.

17. A process in accordance with claim 13, additionally including the step of forming said sulfur ylide compound by the reaction of a sulfoxonium compound with a base in an organic solvent.

* * * * *